United States Patent
Huebel et al.

(10) Patent No.: US 7,316,127 B2
(45) Date of Patent: Jan. 8, 2008

(54) HYDROCARBON GAS PROCESSING FOR RICH GAS STREAMS

(75) Inventors: Robert R. Huebel, Sugar Land, TX (US); Jorge H. Foglietta, Missouri City, TX (US); Sanjiv N. Patel, Sugar Land, TX (US)

(73) Assignee: ABB Lummus Global Inc., Houston, TX (US)

( * ) Notice: Subject to any disclaimer, the term of this patent is extended or adjusted under 35 U.S.C. 154(b) by 446 days.

(21) Appl. No.: 11/102,947

(22) Filed: Apr. 11, 2005

(65) Prior Publication Data

US 2005/0229634 A1 Oct. 20, 2005

Related U.S. Application Data

(60) Provisional application No. 60/562,481, filed on Apr. 15, 2004.

(51) Int. Cl.
*F25J 3/00* (2006.01)
(52) U.S. Cl. .............................. 62/625; 62/628; 62/630; 62/632; 62/636
(58) Field of Classification Search .................. 62/620, 62/625, 628, 630, 632, 636
See application file for complete search history.

(56) References Cited

U.S. PATENT DOCUMENTS

| | | | | |
|---|---|---|---|---|
| 2,225,814 A | * | 12/1940 | Youker | 585/330 |
| 2,855,433 A | * | 10/1958 | Cobb, Jr. | 585/809 |
| 3,446,709 A | * | 5/1969 | Marshall | 196/132 |
| 3,905,873 A | * | 9/1975 | Wright et al. | 202/160 |
| 4,072,604 A | * | 2/1978 | Ward | 208/341 |
| 4,278,457 A | | 7/1981 | Campbell et al. | |
| 5,890,377 A | | 4/1999 | Foglietta | |
| 6,244,070 B1 | | 6/2001 | Lee et al. | |
| 6,401,486 B1 | | 6/2002 | Lee et al. | |
| 7,107,788 B2 | * | 9/2006 | Patel et al. | 62/625 |
| 2002/0157538 A1 | | 10/2002 | Foglietta et al. | |
| 2003/0221447 A1 | | 12/2003 | Mealey | |
| 2004/0148964 A1 | * | 8/2004 | Patel et al. | 62/620 |
| 2004/0159122 A1 | * | 8/2004 | Patel et al. | 62/620 |

* cited by examiner

*Primary Examiner*—William C Doerrler
(74) *Attorney, Agent, or Firm*—McCarter & English, LLP (57) ABSTRACT

A process for the recovery of ethane and heavier hydrocarbon components from a hydrocarbon feed gas stream. Feed gas stream is cooled into a first and second cooled streams. First and second cooled streams are sent to a cold absorber and separated into a first gas stream and a first liquid stream. First gas stream is expanded and sent to a fractionation tower. At least a part of the first liquid stream is sent to a pre-demethanizer stripper tower. Stripper tower produces a stripper overhead stream and a stripper bottoms stream. Stripper overhead vapor stream is cooled and sent to the fractionation tower as second reflux stream. Stripper bottoms stream is supplied to the fractionation tower. Temperatures and pressures of the streams and columns are maintained to recover a major portion of ethane and heavier hydrocarbon components as a bottoms product stream, and produce a residue gas stream at the fractionation tower overhead. At least a portion of the residue gas stream is recycled, cooled and sent to the fractionation tower as first reflux stream.

11 Claims, 3 Drawing Sheets

HYDROCARBON GAS PROCESSING FOR RICH GAS STREAMS

RELATED APPLICATIONS

This application claims the benefit of U.S. Provisional Application Ser. No. 60/562,481 filed Apr. 15, 2004.

TECHNICAL FIELD OF THE INVENTION

The present invention relates to the recovery of ethane and heavier components from hydrocarbon gas streams. More particularly, the present invention relates to the recovery of ethane and heavier components from rich hydrocarbon inlet gas streams.

BACKGROUND OF THE INVENTION

Valuable hydrocarbon components, such as ethane, ethylene, propane, propylene, and heavier hydrocarbon components, are present in a variety of gas streams, such as natural gas streams, refinery off gas streams, coal seam gas streams, and the like. These components can also be present in other sources of hydrocarbons, such as coal, tar sands, and crude oil. The amount of valuable hydrocarbons varies with the feed source. Generally, it is desirable to recover hydrocarbons or natural gas liquids (NGL) from gas streams containing more than fifty percent ethane, carbon dioxide, methane and lighter components, such as nitrogen, carbon monoxide, hydrogen, and the like. Propane, propylene, and heavier hydrocarbon components generally make up a small amount of the inlet gas feed stream.

Figure 1:
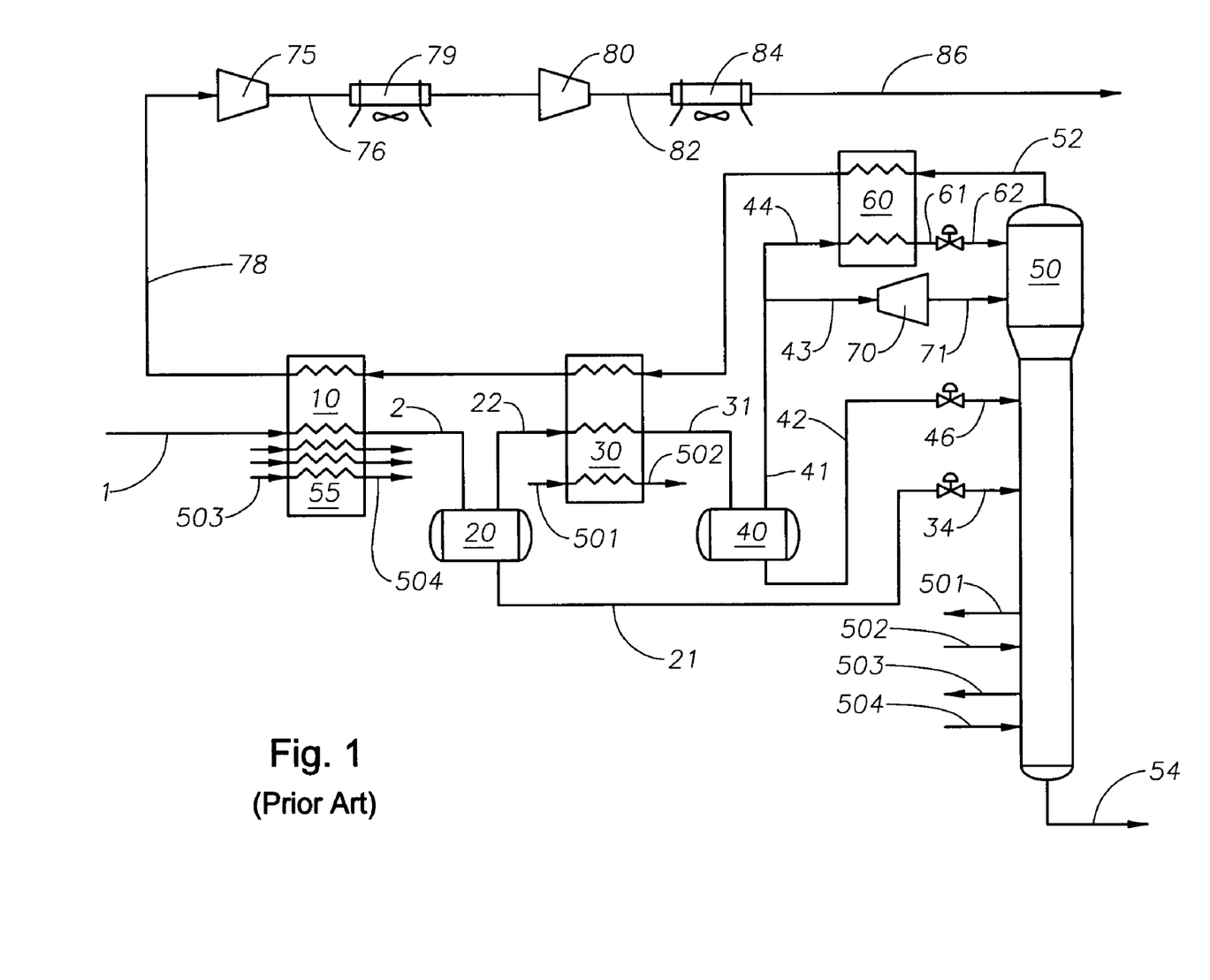
FIG. 1 is a simplified flow diagram of a typical ethane and heavier component recovery process, in accordance with a prior art process as described in U.S. Pat. No. 4,278,457 issued to Campbell.

Several prior art processes exist for the recovery of NGL from hydrocarbon gas streams, such as oil absorption, refrigerated oil absorption, and cryogenic processes to name a few. Because the cryogenic processes are generally more economical to operate and more environmentally friendly, current technology generally favors the use of cryogenic gas processes over oil or refrigerated oil absorption processes. In particular, the use of turboexpanders in cryogenic gas processing is preferred, such as described in U.S. Pat. No. 4,278,457 issued to Campbell, as shown in FIG. 1.

Turboexpander recovery processes that utilize residue recycle streams are capable of obtaining high ethane recoveries (in excess of 95%), while recovering essentially 100% of the C3+ components. Such processes, though impressive in achieving high recoveries, consume relatively large quantities of energy due to their compression requirements. In order to reduce energy consumption while still maintaining high recoveries, an additional source of reflux is needed.

In many cryogenic recovery processes, efficiency is lost due to the quality of the fractionation tower overhead stream, which results in a reflux stream containing a considerable amount of C2+ components. Because the reflux stream has a considerable amount of C2+ components, any flash after a control valve on the reflux stream will lead to some vapor formation. The resulting vapor will have some amount of C2+ components that will escape the fractionation step and be lost in the overhead stream and subsequently in the residue gas stream. Additionally, an equilibrium is reached at the top stage of the fractionation tower that allows more ethane to escape with the overhead stream.

It has been taught to use an absorber to generate lean reflux streams, such as in U.S. Pat. No. 6,244,070 issued to Lee et al. As described in Lee, vapor leaving the inlet separator is split three ways. The first vapor stream is cooled and introduced at the bottom of the absorber column. The second vapor stream is condensed and subcooled and is then introduced at the top of the absorber. The absorber produces an overhead stream that is used as a lean reflux stream for the main fractionation tower. The third vapor stream is sent to the expander for pressure reduction and work extraction. An alternate embodiment proposed by Lee involves using a portion of a high pressure residue gas stream as a top feed stream to the absorber. In this case, vapor exiting the cold separator is split two ways, with one stream being cooled and sent to the bottom of the absorber, while the other stream is sent to the expander. A part of the lean residue gas is condensed under pressure and sent as a top feed stream to the absorber column.

When processing rich gas streams with contents of ethane and heavier components having flow rates of greater than four to five gallons per thousand cubic feet, the initial stages of condensation of liquids containing high amounts of methane occur because of the lean oil effect of the liquids being condensed. This condensation of methane reduces the amount of methane available to produce work during the isoentropic expansion in the turboexpander step of the process. Increased amounts of reflux have to be used to recover the $C_2$ components.

A need exists for an ethane recovery process that is capable of achieving a recovery efficiency of at least 95%, but with lower energy consumption compared to prior art processes. A need also exists for a process that can take advantage of temperature profiles within a process to reduce the amount of C2+ components that are lost in the residue gas streams.

More specifically, a need exists for a $C_2$ and heavier component recovery process from rich gas streams, that is capable of achieving a recovery of at least 95% of ethane and propane and heavier components, that takes advantage of the high amount of methane in the liquid being condensed to create adequate reflux means to recover ethane and also to lower energy consumption compared with prior art processes.

SUMMARY OF THE INVENTION

The present invention advantageously provides a process and apparatus for the recovery of C2+ components from a hydrocarbon stream utilizing a cold absorber, and a pre-demethanizer stripping tower to generate a methane rich reflux stream. The absorber and the pre-demethanizer stripping tower can be separate vessels in a preferred embodiment. These vessels can be combined in one apparatus in another preferred embodiment. In addition, a recycle stream split from a residue gas stream is returned to the process as a residue recycle, or reflux stream, to a fractionation tower. Use of the methane rich reflux stream provides for an ethane recovery in excess of about 96% and a propane recovery in excess of about 99.5% because the methane rich reflux stream contains such a small quantity of the desired products, i.e., the C2+ components.

In accordance with an embodiment of the present invention, a process for separating an inlet gas stream containing methane and lighter components, C2 components, C3 components and heavier hydrocarbons into a more volatile gas fraction containing substantially all of the methane and lighter components and a less volatile hydrocarbon fraction containing a major portion of C2 components, C3 components and heavier hydrocarbons includes the steps of splitting a feed gas stream into a first feed stream and a second feed stream, cooling and partially condensing the first feed stream and the second feed stream to produce a first cooled feed stream and a second cooled feed stream, supplying an absorber tower containing one or more mass transfer stages with the first cooled feed and second cooled feed streams, separating the first and second cooled feed streams in the absorber tower to produce a first vapor stream and a first liquid stream, expanding the first vapor stream to a low pressure so that the first vapor stream forms a lower fractionation tower feed stream, supplying a fractionation tower with the lower fractionation tower feed stream, a first fractionation tower reflux stream, and a second fractionation tower reflux stream, supplying at least a portion of the first liquid stream as a top stripping feed stream to an at least partially reboiled stripping tower that contains one or more mass transfer stages, the at least partially reboiled stripping tower thereby separating the at least a portion of the first liquid stream to produce a stripper overhead stream and a stripper bottoms stream, cooling and thereby substantially condensing the stripper overhead stream to produce the second fractionation tower reflux stream that is sent to the fractionation tower, supplying the fractionation tower with at least a portion of the stripper bottoms stream, separating the at least a portion of the stripper bottoms stream, along with the lower fractionation tower feed stream, the first fractionation tower reflux stream, and the second fractionation tower reflux stream in the fractionation tower to produce a tower bottoms stream and a tower overhead stream, warming the tower overhead stream to produce a residue gas stream, splitting the residue gas stream into a residue recycle stream and a volatile residue gas stream after the step of warming the tower overhead stream to produce the residue gas stream, cooling and thereby substantially condensing the residue recycle stream prior to returning the residue recycle stream to the fractionation tower as the first fractionation tower reflux stream and controlling quantities and temperatures of the first and second fractionation tower reflux streams, lower fractionation tower feed stream, and stripper bottoms stream such that a major portion of the C2 components, C3 components and heavier hydrocarbons is recovered in the tower bottoms stream.

An additional feature of an embodiment of the present invention is that compression of the tower overhead stream occurs after the warming of the tower overhead stream. A further feature of an embodiment of the present invention is that compression of the tower overhead stream includes compressing the tower overhead stream with a compressor having a high pressure stage so that a pressure of the recycle reflux stream can be raised above that of the residue gas stream. A further feature of an embodiment of the present invention is that the C2 recovery in the tower bottoms stream is about 95%. A further feature of an embodiment of the present invention is that the C3 recovery in the tower bottoms stream is about 99%. Another feature of an embodiment of the present invention is that the absorber tower and the at least partially reboiled stripping tower are combined in a single apparatus.

In accordance with an embodiment of the present invention, an apparatus for separating an inlet gas stream containing methane and lighter components, C2 components, C3 components and heavier hydrocarbons into a more volatile gas fraction containing substantially all of the methane and lighter components and a less volatile hydrocarbon fraction containing a major portion of C2 components, C3 components and heavier hydrocarbons includes a means for splitting a feed gas stream into a first feed stream and a second feed stream, at least one first heat exchanger for cooling and partially condensing the first feed stream to produce a first cooled feed stream, at least one second heat exchanger for cooling and partially condensing the second feed stream to produce a second cooled feed stream, an absorber tower containing one or more mass transfer stages for separating the first and second cooled feed streams to produce a first vapor stream and a first liquid stream, an expander for expanding the first vapor stream to a low pressure so that the first vapor stream forms a lower fractionation tower feed stream, an at least partially reboiled stripping tower, the at least partially reboiled stripping tower having one or more mass transfer stages and a top stripping feed stream which includes at least a portion of the first liquid stream, the at least partially reboiled stripping tower thereby separating the at least a portion of the first liquid stream to produce a stripper overhead stream and a stripper bottoms stream, a fractionation tower for separating at least a portion of the stripper bottoms stream, the lower fractionation tower feed stream, a first fractionation tower reflux stream, and a second fractionation tower reflux stream to produce a tower bottoms stream and a tower overhead stream, whereby the quantities and temperatures of the first and second fractionation tower reflux streams, lower fractionation tower feed stream, and stripper bottoms stream are controlled so that a major portion of the C2 components, C3 components and heavier hydrocarbons is recovered in the tower bottoms stream, at least one third heat exchanger for cooling and thereby substantially condensing the stripper overhead stream to produce the second fractionation tower reflux stream and for warming the tower overhead stream to produce a residue gas stream and means for splitting the residue gas stream into a residue recycle stream and a volatile residue gas stream, whereby the residue recycle stream is cooled and thereby substantially condensed in the at least one third heat exchanger prior to returning the residue recycle stream to the fractionation tower as the first fractionation tower reflux stream, and whereby the residue gas stream is split into a residue recycle stream and a volatile residue gas stream after the tower overhead stream has been warmed to produce the residue gas stream.

In accordance with an embodiment of the present invention, a hydrocarbon rich gas feed stream is split in a first gas and second gas feed streams. First gas stream and second gas stream are preferably cooled to at least partially condense the hydrocarbon feed stream. The first gas stream can be cooled in an inlet gas exchanger, and the second gas stream can be cooled in a side reboiler exchanger or other cooler to at least partially condense the hydrocarbon feed stream, thereby forming a first and second cooled feed streams. Other means for cooling the gas streams can be used. Both cooled feed streams are sent to a cold absorber, where the coldest of the two streams is sent to the top section of the cold absorber and the warmer of the two streams is sent to the bottom section of the cold absorber. The separation in the cold absorber is enhanced by both streams having essentially the same chemical composition, but different temperatures. The chemical potential of each stream is different, which provides the driving force to enhance the separation. Cold absorber contains at least one packed bed, or other mass transfer zone, within the absorber vessel. Mass transfer zones can include any type of device that is capable of transferring molecules between a liquid and a gas through contact in the mass transfer zone. Other types of mass transfer zones will be known to those skilled in the art and are to be considered within the scope of the present invention.

The cold absorber produces two streams, a first vapor stream and a first liquid stream. At least a portion of first vapor stream is preferably sent to an expander where its pressure is reduced. Due to this isentropic process, the temperature of the expander exhaust stream, or substantially cooled expanded stream, is substantially reduced. Substantially cooled expanded stream is sent to a fractionation tower, or distillation tower, as a lower tower feed stream. Fractionation tower can be a demethanizer tower. Fractionation tower is preferably a reboiled tower that produces on-specification ethane and heavier components at the bottom of the tower and volatile methane and lighter component streams at the top. Fractionation tower is preferably equipped with side reboilers to improve process efficiency.

At least a portion of first liquid stream is sent to a pre-demethanizer stripping tower, preferably at a top feed location. The pre-demethanizer stripping tower is preferably a reboiled stripping tower. In the pre-demethanizer stripping tower, the first liquid stream is removed or stripped of its methane content by the action of the reboiler. Pre-demethanizer stripping tower is primarily a stripper column preferably containing at least one packed bed, or other mass transfer zone, within the pre-demethanizer stripping tower. Mass transfer zones can include any type of device that is capable of transferring molecules between a liquid and a gas through contact in the mass transfer zone. Other types of mass transfer zones will be known to those skilled in the art and are to be considered within the scope of the present invention.

The pre-demethanizer stripping tower produces two streams, a stripper overhead stream that is rich in methane and stripper bottoms stream. At least a portion of the stripper bottoms stream is sent to the fractionation tower as a second tower feed stream, preferably below the first tower feed stream.

The stripper overhead stream is subcooled and sent to the fractionation tower as a lower tower feed stream, below a first tower reflux feed. The content of methane in the liquid acts as cool lean oil, and absorbs C2+ components from the vapor rising up within the fractionation tower.

The fractionation tower produces a tower overhead stream and tower bottoms stream. Tower overhead stream is preferably warmed and then compressed in compressors to a predefined pressure to produce the residue gas stream. At least a portion of the residue gas stream is taken as reflux and recycled to the fractionation tower as a first tower reflux stream.

This embodiment of the present invention is capable of providing 99+% C2+ recovery. The first tower reflux stream is produced by taking a side stream of the residue gas stream and condensing and subcooling the side stream prior to sending this stream to the fractionation tower as a top tower reflux stream. The residue gas side stream is essentially free of C2+ components, which enables the additional reflux stream to recover any C2+ components that could escape in the tower overhead stream.

BRIEF DESCRIPTION OF THE DRAWINGS

So that the manner in which the features, advantages and objects of the invention, as well as others which will become apparent, may be understood in more detail, more particular description of the invention briefly summarized above may be had by reference to the embodiment thereof which is illustrated in the appended drawings, which form a part of this specification. It is to be noted, however, that the drawings illustrate only a preferred embodiment of the invention and are therefore not to be considered limiting of the invention's scope as it may admit to other equally effective embodiments.

DETAILED DESCRIPTION OF THE DRAWINGS

For simplification of the drawings, figure numbers are the same in the figures for various streams and equipment when the functions are the same or similar, with respect to the streams or equipment, in each of the figures. Like numbers refer to like elements throughout.

As used herein, the term "inlet gas" means a hydrocarbon gas, such gas is typically received from a high-pressure gas line and is substantially comprised of methane, with the balance being C2 components, C3 components and heavier components as well as carbon dioxide, nitrogen and other trace gases. The term "C2 components" means all organic components having two carbon atoms, including aliphatic species such as alkanes, olefins, and alkynes, particularly, ethane, ethylene, acetylene, and the like. The term "C2+ components" means all C2 components and heavier components.

Table I illustrates the composition of a hydrocarbon gas feed stream in which the present invention would be well suited to recover hydrocarbons in accordance with all embodiments of the present invention. Nitrogen and carbon dioxide are considered removed from the compositions to establish an equal base of comparison, since their presence is site specific.

TABLE I

| Component | Mol % |
| --- | --- |
| Methane | 67.41 |
| Ethane | 23.63 |
| Propane | 6.86 |
| n-Butane | 0.43 |
| i-Butane | 1.12 |
| n-Pentane | 0.23 |
| i-Pentane | 0.23 |
| Hexane | 0.05 |
| Heptane+ | 0.05 |

Detailed Description of Prior Art

FIG. 1 illustrates a typical gas processing scheme using turboexpander cryogenic processing, which is an embodiment of the processes described in U.S. Pat. No. 4,278,457 issued to Campbell. Campbell teaches that raw feed gas is treated to remove CO2 and H2S, if they are present in large quantities, prior to processing. The gas is then dried and filtered before being sent to the cryogenic section for NGL recovery. Hydrocarbon feed gas stream 1, which is typically supplied at approximately 100° F. and 800 psia, is cooled against cold process streams in one or more inlet exchangers 10 to approximately −30° F. Depending on the richness of the feed gas stream 1 and feed temperature and pressure, external refrigeration for additional cooling could be needed.

Partially condensed feed gas stream 2 with a temperature of −30° F. is sent to an intermediate separator 20 for vapor-liquid or phase separation. Depending on the feed gas stream composition, one or more cooling steps may be required with vapor liquid separation in between the cooling steps. Cooled feed gas stream 2 is separated into a first liquid stream 21 and a first vapor stream 22. First liquid stream 21 is richer in methane, ethane, ethylene, propane, propylene and heavier hydrocarbon components, than inlet feed gas stream 1. First liquid stream 21 is sent to a fractionation tower 50 for recovery of the valuable C2+ components. Prior to being sent to fractionation tower 50, first liquid stream 21 is expanded across a control valve to essentially a fractionation tower pressure. Due to this expansion of liquid, some liquid is vaporized, thereby cooling the entire stream 34 and producing a two-phase stream at approximately −75° F. that is sent to the fractionation tower 50.

First vapor stream 22 is sent to exchanger 30 where it is cooled to −60° F. and partially condensed to produce stream 31 and sent to the cold separator 40. After separation of phases in separator 40, two streams are produced, second vapor stream 41 and second liquid stream 42. Second vapor stream 41 is split in two streams, first gas stream 43 and second gas stream 44. First gas stream 43 is sent through a work expansion machine 70, such as a turboexpander, where the pressure of first gas stream 43 is reduced to approximately 295 psia. Due to isentropic expansion of first gas stream 43, the pressure and temperature of first gas stream 43 is reduced. Due to this reduction in pressure and extraction of work, the temperature of first gas stream 43 drops to approximately −121° F., which leads to liquid formation. This two-phase stream 71 is sent to the fractionation tower 35 as a middle feed stream. Work generated by the turboexpander 70 is used to boost up a lean tower overhead stream 52 to produce residue gas stream 86.

Second gas stream 44 is sent to a reflux exchanger 60, where second gas stream 44 is condensed and subcooled to approximately −128° F. to produce a first tower feed stream 61. First tower feed stream 61 is then flashed across an expansion device, such as a control valve, to essentially fractionation tower pressure. The reduction in pressure of first tower feed stream 61 leads to vapor formation and a reduction of temperature to approximately −152° F. This two phase stream 62 is sent to fractionation tower 50 as a top feed stream.

Second liquid stream 42 is sent to fractionation tower 50 for recovery of the valuable C2+ components. Prior to being sent to fractionation tower 50, first liquid stream 42 can be expanded across a control valve to essentially a fractionation tower pressure and consequently cooled to approximately −112° F. Due to this expansion of liquid, some liquid is vaporized, thereby cooling the entire stream 46 and producing a two-phase stream that is sent to the fractionation tower 50.

Fractionation tower 50 preferably is a reboiled absorber that produces a tower bottoms stream 54, which contains a larger part of the C2+ components or NGL in the inlet feed gas stream 1, and a tower overhead stream 52, which contains the remaining ethane, methane and lighter components. Fractionation tower 50 preferably includes a reboiler 55 fed by sidestream 501 and 503 to control the amount of methane that exits tower 50 with the NGL in tower bottoms stream 54. To further enhance the efficiency of the process, one or more side reboilers can be provided that cool inlet feed gas stream 1. Depending on the feed richness and delivery conditions, some external heating for fractionation tower 50 could be required, as well as refrigeration to aid in the cooling process. Such refrigeration could be supplied by a propane refrigeration system, for example.

Tower overhead stream 52, which typically has a pressure of approximately 290 psia and a temperature of approximately −139° F., is warmed in reflux exchanger 60 to approximately −60° F., and then to 95° F. in inlet exchanger 10 to produce a warmed overhead tower stream 78. Warmed overhead tower stream 78 is sent to the booster compressor 75 where its pressure is raised to approximately 297 psia using work generated by expander 70 to produce compressed overhead gas stream 76. Compressed overhead gas stream 76 is then cooled to approximately 100° F. in an air cooler 79 and sent for further compression in recompressor 80 to approximately 810 psia to produce warm residue gas stream 82. Warm residue gas stream 82 is then cooled in air cooler 84 to approximately 100° F. and is then sent for further processing as residue gas stream 86.

A simulation was performed using the prior art process described herein and illustrated in FIG. 1. The molar composition of several process streams are provided in Table II for comparison purposes.

Table II for Process in FIG. 1
PRIOR ART PROCESS

| Component | Mol % | | | |
|---|---|---|---|---|
| | Feed (1) | Reflux (62) | Overhead (52) | NGL (54) |
| Methane | 67.41 | 88.64 | 97.45 | 0.95 |
| Ethane | 23.63 | 10.49 | 2.54 | 70.29 |
| Propane | 6.86 | 0.82 | 0.01 | 22.01 |
| n-Butane | 0.43 | 0.02 | 0.00 | 1.38 |
| i-Butane | 1.12 | 0.03 | 0.00 | 3.58 |
| n-Pentane | 0.23 | 0.00 | 0.00 | 0.74 |
| i-Pentane | 0.23 | 0.00 | 0.00 | 0.74 |
| Hexane | 0.05 | 0.00 | 0.00 | 0.16 |
| Heptane+ | 0.05 | 0.00 | 0.00 | 0.16 |
| Mol/hr | 54902 | 11958 | 37813 | 17089 |
| Temperature (° F.) | 100.0 | −151.2 | −139.0 | 40.8 |
| Pressure (psia) | 800 | 295 | 290 | 295 |
| C2 Recovery (%) | | | 92.6 | |
| C3 Recovery (%) | | | 99.85 | |
| Liquids recovered, gpm | | | 2907 | |
| Residue Compression (hp) | | | 23,230 | |
| Refrig. Compression (hp) | | | 15,920 | |
| Specific energy, hp/gpm | | | 13.48 | |

Description of the Present Invention

Figure 2:
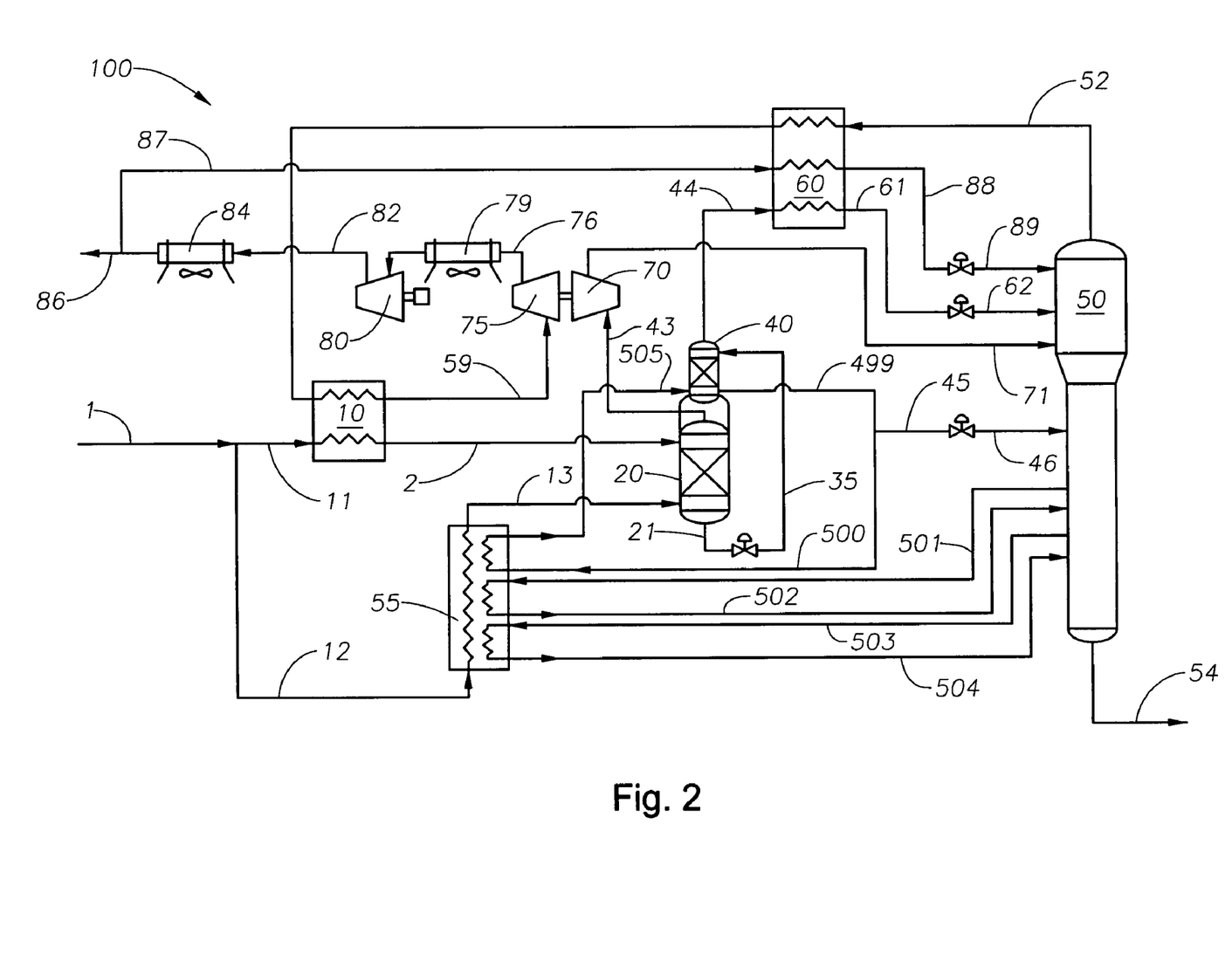
FIG. 2 is a simplified flow diagram of an ethane and heavier component recovery process that utilizes a cold absorber and a pre-demethanizer stripping tower according to an embodiment of the present invention.

The present invention advantageously provides a process for separating an inlet feed gas stream containing methane and lighter components, C2 components, C3 components and heavier hydrocarbons from rich gas streams, into a more volatile gas fraction containing substantially all of the methane and lighter components and a less volatile hydrocarbon fraction containing a major portion of C2 components, C3 components and heavier hydrocarbons, as shown in FIG. 2.

More specifically, a feed gas stream 1 is supplied that has preferably been filtered and dried prior to being sent to this ethane recovery process 100. Feed gas stream 1 can contain certain impurities, such as water, carbon monoxide, and hydrogen sulfide, which are removed prior to being sent to ethane recovery process 100. Feed gas stream 1 preferably has a temperature of approximately 100° F. and a pressure of approximately 800 psia. Once supplied to process 100, feed gas stream 1 is preferably split into a first feed stream 11, which contains approximately 62% of feed gas stream 1, and a second feed stream 12, which contains the remaining portion of feed gas stream 1. First feed stream 11 can be cooled and partially condensed in inlet exchanger 10 by heat exchange contact with at least tower overhead stream 52 or other suitable stream to produce a cooled first feed stream 2 having a temperature of approximately −53° F. Second feed stream 12 can be cooled in a reboiler 55 by heat exchange contact with at least first tower sidestream 501, second tower sidestream 503, or combinations thereof to produce cooled second feed stream 13 having a temperature of approximately −50° F. Second cooled feed stream 13 and first cooled stream 2 are sent to cold absorber 20, with the coldest of the two steams being sent to the top of the absorber 20 and the warmest of the two streams being sent to the bottom of the absorber 20. The separation in the cold absorber 20 is enhanced by both streams having the same composition but different temperatures. Their chemical potential is different, which provides the driving force to enhance the separation. Cold absorber 20 contains at least one packed bed, or other mass transfer zone, within the absorber vessel 20. Mass transfer zones can include any type of device that is capable of transferring molecules from a liquid flowing down the vessel containing the mass transfer zone to a gas rising through the vessel and from the gas rising through the vessel to the liquid flowing down the vessel. Other types of mass transfer zones will be known to those skilled in the art and are to be considered within the scope of the present invention.

Two streams leave the cold absorber, first vapor stream 43 and first liquid stream 21. First vapor stream 43 is advantageously sent to expander 70 where the stream is expanded to a lower pressure of approximately 405 psia to produce lower tower feed stream 71. Due to the reduction in pressure in first vapor stream 43 and extraction of work, the temperature of lower feed stream 71 is also reduced to approximately −97° F. The decrease in temperature causes liquid formation, which causes tower feed stream 71 to be two-phased. Tower feed stream 71 is sent to a fractionation tower 50 preferably as a lower tower feed stream.

Lower tower feed stream 71, along with a first tower feed stream 46, is sent to fractionation tower 50 where the streams are separated into a tower bottoms stream 54 and a tower overhead stream 52. Tower overhead stream 52 is warmed and compressed to produce a residue gas stream 86.

At least a portion of first liquid stream 21 is sent to pre-demethanizer stripping tower 40 as a top stripper feed stream. Pre-demethanizer stripping tower 40 preferably contains one or more mass transfer stages. In the pre-demethanizer stripping tower 40, the high methane content liquid is at least partially reboiled to remove the methane. In one embodiment, the reboiling action could be achieved by contacting liquid 500 from the stripping tower with second feed stream 12 in reboiler 55, and returning stream 505 to the stripping tower. Warm vapor rising to the top of stripping tower 40 intimately contacts the cold, heavier liquids flowing down stripping tower 40. The warm vapors strip the lighter liquids from the liquid stream. Stripping tower 40 preferably produces stripper overhead stream 44 and stripper bottoms stream 45. Other sources of heat or stripping vapor are encompassed in the invention.

Stripper overhead stream 44 preferably has a temperature of approximately −62° F. and is much leaner than reflux stream 44 in the prior art process shown in FIG. 1. Stripper overhead stream 44 is then cooled to approximately −128° F. and thereby substantially condensed in reflux exchanger 60 by heat exchange contact with at least tower overhead stream 52 to produce second tower reflux stream 62.

Fractionation tower 50, or demethanizer, is preferably a reboiled absorber tower type that produces tower bottoms stream 54 and tower overhead stream 52. Tower bottoms stream 54 contains a larger part of the C2+ components, or NGL, in the inlet feed gas stream 1. Tower overhead stream 52 contains the remaining ethane, methane and lighter components. Fractionation tower 50 preferably includes a reboiler 55 operable to control the amount of methane that leaves with the NGL in tower bottoms stream 54. To further enhance the efficiency of the process, one or more side reboilers can be provided to cool inlet feed gas stream 12 and aid in the condensation of high pressure feed gas stream 13, along with increasing the efficiency of the process. Depending on the feed richness and delivery conditions, some external heating for fractionation tower 50 could be desirable, as well as refrigeration to aid in the cooling process. Such refrigeration could be supplied by a propane refrigeration system, for example.

In a preferred embodiment, a plurality of reflux streams 501, 503 are removed from a lower portion of fractionation tower 50, heated in reboiler 55 by heat exchange contact with second feed stream 12, and are returned to the fractionation tower 50 just below the location from which they were removed.

Tower overhead stream 52, which typically has a pressure of approximately 400 psia and a temperature of approximately −134° F., is warmed in reflux exchanger 60 to approximately −62° F., and then to 95° F. in inlet exchanger 10 to produce a warmed overhead tower stream 59. Warmed overhead tower stream 59 is sent to the booster compressor 75 where its pressure is raised to approximately 420 psia to produce compressed overhead gas stream 76 using work generated by expander 70. Compressed overhead gas stream 76 is then cooled to approximately 100° F. in air cooler 79 and sent for further compression in recompressor 80 to approximately 800 psia to produce warm residue gas stream 82. Warm residue gas stream 82 is then cooled in air cooler 84 to approximately 100° F. and is then sent for further processing as residue gas stream 86.

As described herein, the prior art process shown in FIG. 1 has limitations on the maximum ethane recovery due to equilibrium conditions at the top of fractionation tower 50. To overcome this limitation, the present invention reduces the amount of C2+ components in the reflux stream returning to fractionation tower 50, which enables higher recoveries since fewer C2+ components are in the tower overhead stream 52.

The current invention overcomes this limitation by removing a portion of residue gas stream 86 to create a residue recycle stream 87. Residue recycle stream 87 is cooled to approximately −128° F. and thereby substantially condensed prior to returning to fractionation tower 50; preferably at a top feed location. Because residue recycle stream 89 essentially contains no C2+ components, residue recycle stream 89 is a good source of top reflux for fractionation tower 50. Quantities and temperatures of the first and second tower feed streams 89 and 62, respectively, are maintained so that a tower overhead temperature of the tower overhead stream 52 is maintained and a major portion of the C2 components, C3 components and heavier hydrocarbons is recovered in the tower bottoms stream 54.

A simulation was performed using the process according to a first embodiment of the present invention. The molar composition of several process streams is provided in Table III for comparison purposes to the results related to the prior art process in Table II.

Table III for Process in FIG. 2 PRESENT INVENTION

| Component | Feed (1') | Reflux (89) | Residue (86) | NGL (54) |
|---|---|---|---|---|
| | | Mol % | | |
| Methane | 67.41 | 97.36 | 97.35 | 1.11 |
| Ethane | 23.63 | 1.68 | 1.70 | 70.67 |
| Propane | 6.86 | 0.01 | 0.01 | 21.60 |
| n-Butane | 0.43 | 0.00 | 0.00 | 1.35 |
| i-Butane | 1.12 | 0.00 | 0.00 | 3.51 |
| n-Pentane | 0.23 | 0.00 | 0.00 | 0.72 |
| i-Pentane | 0.23 | 0.00 | 0.00 | 0.72 |
| Hexane | 0.05 | 0.00 | 0.00 | 0.16 |
| Heptane+ | 0.05 | 0.00 | 0.00 | 0.16 |
| Mol/hr | 54902 | 10495 | 37440 | 17462 |
| Temperature (° F.) | 100.0 | −145.0 | −133.8 | 67 |
| Pressure (psia) | 800 | 405 | 400 | 405 |
| C2 Recovery (%) | | 95.1 | | |
| C3 Recovery (%) | | 99.9 | | |
| Liquids Recovered, gpm | | 3008 | | |
| Residue/Recycle Compr. (hp) | | 19054 | | |
| Refrig. Compression, (hp) | | 16670 | | |
| Specific energy, hp/gpm | | 11.87 | | |

By comparing Tables II and III, it is evident that the process of the present invention generates a much leaner reflux stream, thereby leading to higher recoveries of C2+ components than in the prior art process shown in FIG. 1.

Table IV illustrates an economic comparison between the process schemes shown in FIGS. 1 and 2. Based on current assumed prices of products and natural gas, the process scheme in FIG. 2 in accordance with an embodiment of the present invention recovers higher amounts of desired components.

TABLE IV

| | FIG. 1 | FIG. 2 | Difference | Price $/BBL $/MMBTU | $/Day |
|---|---|---|---|---|---|
| C2 (BPD) | 69536 | 71786 | 2250 | 18.9 | 42,525 |
| C3 (BPD) | 22413 | 22528 | 115 | 24.7 | 2,840 |
| Residue (MMSCFD) | 344.4 | 340.9 | −3.5 | 5 | −17,500 |
| Compression (hp) | 39300 | 35724 | −3576 | 5 | 3,442 |
| | | | Increase in Revenue | | 31,307 |
| | | | Turbine Cost (MM$) Savings | | 1,788,000 |
| | | | Net Revenue Increase (MM$/yr) | | 11.427 |

Turbine Cost: $500/hp
Turbine heat rate 8000 BTU/hp-hr

Figure 3:
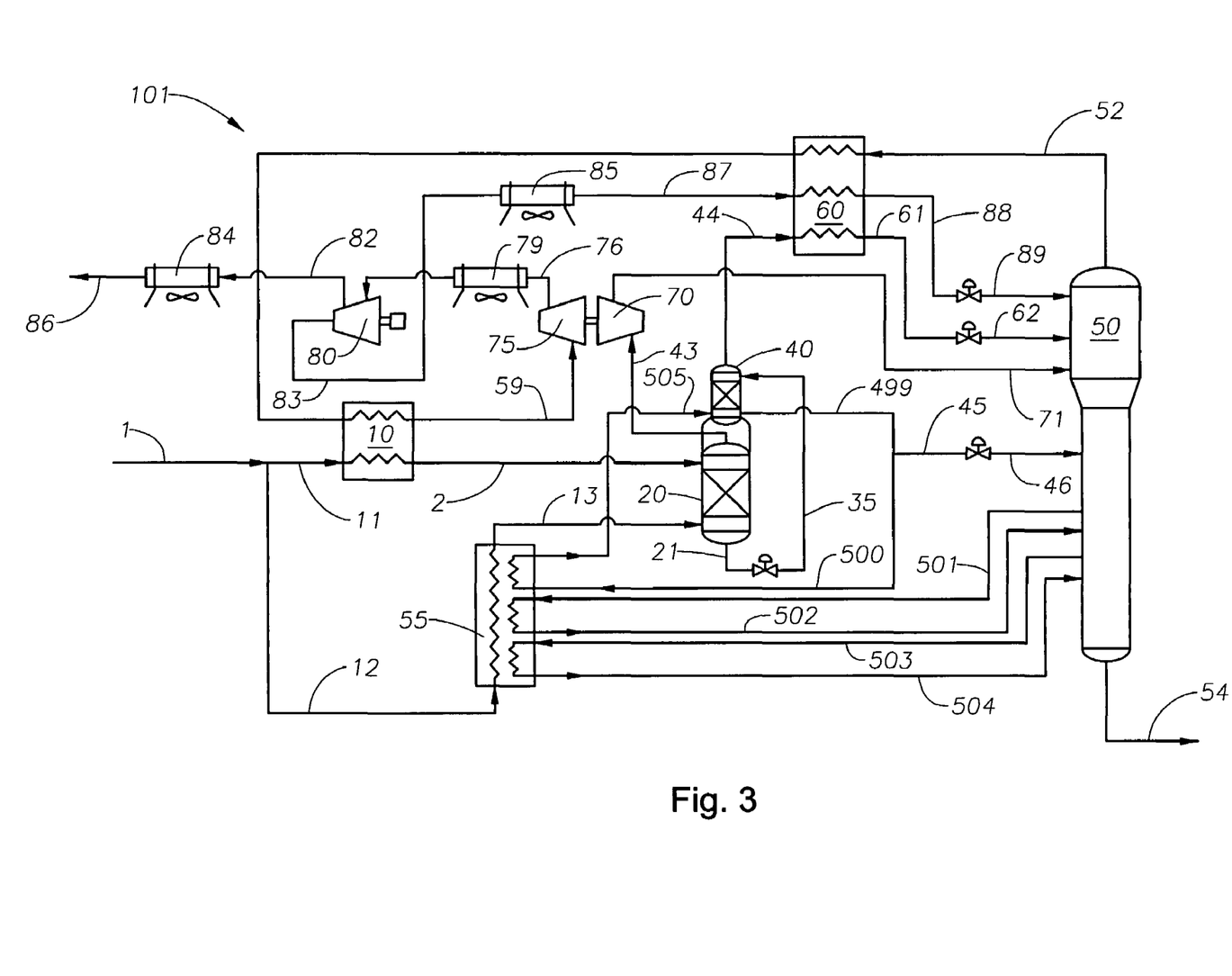
FIG. 3 is a simplified flow diagram of an ethane and heavier component recovery process utilizing a cold absorber and a pre-demethanizer stripping tower, along with a high stage compressor for boosting the pressure of the residue recycle stream in accordance with an embodiment of the present invention.

FIG. 3 depicts another preferred embodiment of the present invention. FIG. 3 shows an ethane recovery process 101 in which compressor 80 has an additional high pressure stage, or a separate high pressure stage, to raise the pressure of the recycle reflux stream 87 above that of the residue gas stream 86. If the residue recycle stream does not have enough pressure to fully or substantially condense when cooled prior to being returned to fractionation tower 50, then this embodiment can be used to at least substantially condense recycle reflux stream 87.

In addition to the process embodiments of the present invention, the apparatus used to perform the processes described herein is advantageously provided. The apparatus used to perform the processes described herein is shown in FIGS. 2 and 3.

As an advantage of the present invention, the present invention can achieve high ethane and high propane recoveries, while realizing a significant cost savings with respect to operating costs. The high condensation of methane within the reflux streams returned to the fractionation tower helps achieve high recovery rates, while simultaneously reducing the compression requirements, which results in a substantial costs savings.

While the invention has been shown or described in only some of its forms, it should be apparent to those skilled in the art that it is not so limited, but is susceptible to various changes without departing from the scope of the invention.

For example, the expanding steps, preferably by isentropic expansion, can be effectuated with a turbo-expander, Joule-Thompson expansion valves, a liquid expander, a gas or vapor expander or the like. As another example, the mass transfer zone can be a tray or similar equilibrium separation stage a flash vessel, or the like.

We claim:

1. A process for separating an inlet gas stream containing methane and lighter components, C2 components, C3 components and heavier hydrocarbons into a more volatile gas fraction containing substantially all of the methane and lighter components and a less volatile hydrocarbon fraction containing a major portion of C2 components, C3 components and heavier hydrocarbons, the process comprising the steps of:

splitting a feed gas stream into a first feed stream and a second feed stream;

cooling and partially condensing the first feed stream and the second feed stream to produce a first cooled feed stream and a second cooled feed stream;

supplying an absorber tower containing one or more mass transfer stages with the first cooled feed and second cooled feed streams;

separating the first and second cooled feed streams in the absorber tower to produce a first vapor stream and a first liquid stream;

expanding the first vapor stream to a low pressure so that the first vapor stream forms a lower fractionation tower feed stream;

supplying a fractionation tower with the lower fractionation tower feed stream, a first fractionation tower reflux stream, and a second fractionation tower reflux stream;

supplying at least a portion of the first liquid stream as a top stripping feed stream to an at least partially reboiled stripping tower that contains one or more mass transfer stages, the at least partially reboiled stripping tower thereby separating the at least a portion of the first liquid stream to produce a stripper overhead stream and a stripper bottoms stream;

cooling and thereby substantially condensing the stripper overhead stream to produce the second fractionation tower reflux stream that is sent to the fractionation tower;

supplying the fractionation tower with at least a portion of the stripper bottoms stream;

separating the at least a portion of the stripper bottoms stream, along with the lower fractionation tower feed stream, the first fractionation tower reflux stream, and the second fractionation tower reflux stream in the fractionation tower to produce a tower bottoms stream and a tower overhead stream;

warming the tower overhead stream to produce a residue gas stream;

splitting the residue gas stream into a residue recycle stream and a volatile residue gas stream after the step of warming the tower overhead stream to produce the residue gas stream;

cooling and thereby substantially condensing the residue recycle stream prior to returning the residue recycle stream to the fractionation tower as the first fractionation tower reflux stream; and controlling quantities and temperatures of the first and second fractionation tower reflux streams, lower fractionation tower feed stream, and stripper bottoms stream such that a major portion of the C2 components, C3 components and heavier hydrocarbons is recovered in the tower bottoms stream.

2. The process of claim 1, wherein the process further comprises the step of compressing the tower overhead stream after the step of warming the tower overhead stream.

3. The process of claim 2, wherein the step of compressing the tower overhead stream includes compressing the tower overhead stream with a compressor having a high pressure stage so that a pressure of the recycle reflux stream can be raised above that of the residue gas stream.

4. The process of claim 1, whereby the C2 recovery in the tower bottoms stream is about 95%.

5. The process of claim 1, whereby the C3 recovery in the tower bottoms stream is about 99%.

6. The process of claim 1, further comprising the absorber tower and the at least partially reboiled stripping tower combined in a single apparatus.

7. An apparatus for separating an inlet gas stream containing methane and lighter components, C2 components, C3 components and heavier hydrocarbons into a more volatile gas fraction containing substantially all of the methane and lighter components and a less volatile hydrocarbon fraction containing a major portion of C2 components, C3 components and heavier hydrocarbons, the apparatus comprising:

a means for splitting a feed gas stream into a first feed stream and a second feed stream;

at least one first heat exchanger for cooling and partially condensing the first feed stream to produce a first cooled feed stream;

at least one second heat exchanger for cooling and partially condensing the second feed stream to produce a second cooled feed stream;

an absorber tower containing one or more mass transfer stages for separating the first and second cooled feed streams to produce a first vapor stream and a first liquid stream;

an expander for expanding the first vapor stream to a low pressure so that the first vapor stream forms a lower fractionation tower feed stream;

an at least partially reboiled stripping tower, the at least partially reboiled stripping tower having one or more mass transfer stages and a top stripping feed stream which includes at least a portion of the first liquid stream, the at least partially reboiled stripping tower thereby separating the at least a portion of the first liquid stream to produce a stripper overhead stream and a stripper bottoms stream;

a fractionation tower for separating at least a portion of the stripper bottoms stream, the lower fractionation tower feed stream, a first fractionation tower reflux stream, and a second fractionation tower reflux stream to produce a tower bottoms stream and a tower overhead stream, whereby the quantities and temperatures of the first and second fractionation tower reflux streams, lower fractionation tower feed stream, and stripper bottoms stream are controlled so that a major portion of the C2 components, C3 components and heavier hydrocarbons is recovered in the tower bottoms stream;

at least one third heat exchanger for cooling and thereby substantially condensing the stripper overhead stream to produce the second fractionation tower reflux stream and for warming the tower overhead stream to produce a residue gas stream; and means for splitting the residue gas stream into a residue recycle stream and a volatile residue gas stream;

whereby the residue recycle stream is cooled and thereby substantially condensed in the at least one third heat exchanger prior to returning the residue recycle stream to the fractionation tower as the first fractionation tower reflux stream, and whereby the residue gas stream is split into a residue recycle stream and a volatile residue gas stream after the tower overhead stream has been warmed to produce the residue gas stream.

8. The apparatus of claim 7, further comprising a compressor for compressing the tower overhead stream after the step of warming the tower overhead stream.

9. The apparatus of claim 8, wherein the compressor has a high pressure stage so that a pressure of the recycle reflux stream can be raised above that of the residue gas stream.

10. The apparatus of claim 7, whereby the C2 recovery in the tower bottoms stream is about 95%.

11. The apparatus of claim 7, whereby the C3 recovery in the tower bottoms stream is about 99%.

* * * * *